United States Patent
Nordmeyer et al.

(10) Patent No.: US 12,078,331 B2
(45) Date of Patent: Sep. 3, 2024

(54) COMPACT LIGHTING SYSTEM INCLUDING LEDS ELECTRICALLY CONNECTED TO HEAT SINKS

(71) Applicant: LumeNXT LLC, Boston, MA (US)

(72) Inventors: Michael Nordmeyer, Boston, MA (US); Robin S. Horrell, Boston, MA (US); Jose Fernandez, Boston, MA (US)

(73) Assignee: LumeNXT, LLC, Knoxville, TN (US)

( * ) Notice: Subject to any disclaimer, the term of this patent is extended or adjusted under 35 U.S.C. 154(b) by 0 days.

(21) Appl. No.: 18/038,841

(22) PCT Filed: Jul. 8, 2021

(86) PCT No.: PCT/US2021/040801
§ 371 (c)(1),
(2) Date: May 25, 2023

(87) PCT Pub. No.: WO2022/011085
PCT Pub. Date: Jan. 13, 2022

(65) Prior Publication Data
US 2024/0019112 A1 Jan. 18, 2024

Related U.S. Application Data

(60) Provisional application No. 63/049,199, filed on Jul. 8, 2020.

(51) Int. Cl.
*A61B 1/12* (2006.01)
*A61B 1/06* (2006.01)
(Continued)

(52) U.S. Cl.
CPC .......... *F21V 23/002* (2013.01); *A61B 1/0684* (2013.01); *A61B 1/128* (2013.01);
(Continued)

(58) Field of Classification Search
CPC .. A61B 1/06; A61B 1/12; A61B 1/128; A61B 90/30; A61B 90/36; F21V 29/503;
(Continued)

(56) References Cited

U.S. PATENT DOCUMENTS 4,967,330 A * 10/1990 Bell ..................... F21V 29/83
362/373
6,517,218 B2 * 2/2003 Hochstein ............. F21V 29/713
362/800
(Continued)

FOREIGN PATENT DOCUMENTS

WO 2020245817 A1 12/2020

*Primary Examiner* — Ismael Negron
(74) *Attorney, Agent, or Firm* — Shane P. Coleman (57) ABSTRACT

A lighting system includes a plurality of LEDs at least two heat sinks electrically connected to the LEDs, an insulator separating the heat sinks, a lens assembly provided opposite the heat sinks from the LEDs, and a power source. One of the heat sinks includes a recess, with the other of the heat sinks configured to be nested in the recess, such that the outer perimeters of both heat sinks align. The electrodes of the LEDs are connected to a corresponding one of the heat sinks, and forming a circuit with the power source.

16 Claims, 6 Drawing Sheets

(51) Int. Cl.
*F21V 23/00* (2015.01)
*F21V 29/503* (2015.01)
*F21V 29/70* (2015.01)
*F21W 131/205* (2006.01)
*F21Y 115/10* (2016.01)

(52) U.S. Cl.
CPC ............ *F21V 29/503* (2015.01); *F21V 29/70* (2015.01); *F21W 2131/205* (2013.01); *F21Y 2115/10* (2016.08)

(58) Field of Classification Search
CPC .......................... F21V 29/70; F21W 2131/205; F21Y 2115/10
See application file for complete search history.

(56) References Cited

U.S. PATENT DOCUMENTS

| | | | | |
|---|---|---|---|---|
| 6,541,800 B2* | 4/2003 | Barnett | ................ | H01L 33/642 257/E33.059 |
| 6,827,468 B2* | 12/2004 | Galli | ...................... | F21S 45/47 362/555 |
| 6,903,382 B2* | 6/2005 | Ho | .......................... | H01L 33/52 257/E33.059 |
| 7,618,155 B2* | 11/2009 | Chen | ...................... | F21V 29/80 362/202 |
| 7,652,303 B2* | 1/2010 | Galli | ...................... | F21V 29/75 257/676 |
| 7,674,015 B2* | 3/2010 | Chien | .................... | F21K 9/233 257/722 |
| 8,071,997 B2 | 12/2011 | Scotch et al. | | |
| 8,459,844 B2* | 6/2013 | Lia | .......................... | A61B 1/06 362/326 |
| 9,927,113 B2* | 3/2018 | Birnkrant | ................ | H01L 33/62 |
| 10,174,912 B1* | 1/2019 | Ferguson | ............. | F21V 23/002 |
| 2006/0291195 A1 | 12/2006 | Horrell et al. | | |
| 2008/0266840 A1 | 10/2008 | Nordmeyer et al. | | |
| 2011/0012534 A1* | 1/2011 | West | ...................... | F21L 4/027 315/307 |
| 2011/0012535 A1* | 1/2011 | West | ...................... | F21L 4/005 315/307 |
| 2017/0343203 A1 | 11/2017 | Birnkrant | | |

\* cited by examiner

COMPACT LIGHTING SYSTEM INCLUDING LEDS ELECTRICALLY CONNECTED TO HEAT SINKS

CROSS REFERENCE TO RELATED APPLICATIONS

This application claims priority to U.S. Provisional Application No. 63/049,199 filed on Jul. 8, 2020 entitled COMPACT LIGHTING SYSTEM INCLUDING LEDS ELECTRICALLY CONNECTED TO HEAT SINKS, the contents of which are herein incorporated by reference in their entirety.

FIELD OF THE INVENTION

The invention generally relates to the field of medical and surgical devices, and more particularly relates to a lighting device, which disperses heat from the lighted tip. The invention also relates to a lightweight, compact lighting system configured to provide lighting of a surgical site. Another element is a low heat lighting system such as light emitting diodes (LEDs). Heat incidental to generation of light is removed away from the light-generating portion of the lighting system to ensure safe prolonged operation.

BACKGROUND OF THE INVENTION

Light-emitting-diode (LED) lamps are known in the art. A LED lamp is a lamp that uses LEDs as the source of light. In such lamps, multiple diodes may be used for e.g. for increasing the output power of the lamp or for providing a white light when utilizing LEDs that emit light in a narrow band of wavelengths (as opposed to for instance using phosphor converted LEDs, which may emit light in the whole visible spectrum, thereby providing a more-or-less white light). LED lamps may be used for general lighting or even more specific lighting as the color and the output power may be tuned.

Ambient illumination is often inadequate for conducting safe and efficacious medical examinations and surgical procedures. Regardless of the intensity of the ambient lighting, shadows cast by medical personnel and/or other objects in a room (e.g., draperies or overlying patient's own tissues) may prevent proper illumination of an examination site or surgical site. Moreover, when a surgical procedure is conducted inside a body cavity, providing sufficient lighting is even more difficult to achieve.

Illumination devices inserted into body cavities must be safe, reliable, capable of being sterilized, capable of operating with other surgical instruments, and be easy for a physician to manipulate. Critical specification features for such illumination devices typically include the brightness of the light, the amount of heat generated by the light, battery life, the shelf life of the device, ease of use with and without other devices, and affordability. For example, a light source may generate excessive heat that causes tissue damage a patient, ignite draperies or injures a member of a medical team. Thus, it is desirable to have an illumination device that efficiently removes heat from the light source to avoid excessive temperatures that may damage tissue or injure medical personnel.

Applying clear white light of sufficient intensity for periods exceeding more than a few minutes poses the problem that portions of the lighting system may attain unacceptably high local temperature and may accidentally cause tissue damage to either the patient or to members of the surgical team. Another concern always present if oxygen is being supplied to the patient is the danger of igniting materials contacted by the light source.

Placing the light emission source as close to the surgeon's visual target obviates the need for extra components to transmit light emitted from elsewhere. Being able to locate the source reduces device cost directly via fewer components and indirectly through lower engineering and assembly cost. A closer source location moves heat generation deeper into the wound and makes the need for heat dissipation strategies more important.

In addition to illuminating a space, or cavity, light sources may also be used for transillumination of a tissue. Specifically, a light is shone through tissue to help visualize deeper elements within the tissue, such as blood vessels, connective tissue, nerves, etc. Heat removal from the transilluminated source is especially important because the light source or device is often pressed directly against the tissue for long periods of time, while a surgeon dissects towards the light.

Light emitting diodes (LEDs) are well known solid state light sources. LEDs have many advantages over traditional sources such as incandescent bulbs as they are cheaper to produce, more robust, and require less power. LEDs are especially desirable as they emit light with high power efficiency over specific colors in the spectrum. However, LEDs suffer from the same tradeoff that exists for other illumination sources, whereby increased energy is required for increased illumination. LEDs are favored in this application because the light output produced per unit of power applied is greater than other incandescent sources.

Regardless, heat is still produced in proportion to the light output. Heat generation per unit surface area goes up at the same light output as small LED are used to do the same job. This means local hot spots which are hotter in the same application with smaller devices. Since an LED is a semiconductor device, the greater heat effects the semi-conductor characteristics of the LED. Relatively high heat levels may cause a degradation of performance in the form of unpredictable light color change or loss, or, worse, a catastrophic break down in the semi-conductor material resulting in failure of the LED.

Although LEDs are considerably cooler than other light sources, a need still exists to remove heat from the distal end of the light system and dissipate or draw the heat away from the surgical site in order to keep the site cool.

A heat sink is a component providing a large surface for radiating and convection of heat away from the LED devices. In a typical design, the heat sink is a relatively massive metal element having a large engineered surface area, for example by having fins or other heat dissipating structures on its outer surface. The large mass of the heat sink efficiently conducts heat from the LED devices to the heat fins, and the large area of the heat fins provides efficient heat egress by radiation and convection. The heat sink may also be in contact with other elements of the mechanical system and effectively increase or extend the efficiency of the heat sink. Thoughtfully developed devices like the one described herein take advantage of this property. For high power LED-based lamps it is also known to employ active cooling using fans or synthetic jets or heat pipes or thermoelectric coolers or pumped coolant fluid to enhance the heat removal. Heat sinks are thermally connected to the LED but are electrically isolated.

In the case of incandescent, halogen, and HID light sources, all of which are thermal emitters of light, the heat transfer to the air space proximate to the lamp is managed by design of the radiative and convective thermal paths in order to achieve an elevated target temperature during operation of the light source. In contrast, in the case of LED light sources, photons are not thermally-excited, but rather are generated by recombination of electrons with holes at the p-n junction of a semiconductor. Both the performance and the life of the light source are optimized by minimizing the operating temperature of the p-n junction of the LED, rather than operating at an elevated target temperature. By providing a heat sink with increased mass, fins and/or other surface area-increasing structures, the surface for convective and radiative heat transfer is enhanced.

Heat sinks have been used to help draw the heat away but have remained only thermally coupled to the light source, which may increase the bulk of the light system, and be less efficient in dissipating the heat. A heat sink thermally coupled to the light source utilizes low or non-conductive materials to draw the heat in order to prevent shorting the power source. Reducing the elements connecting the LED to the heat sink allows for a more efficient way to remove heat from the space near the LED.

The LED is powered through a pair of electrically conductive leads. These leads are often coincident with the optimum location for removal of heat. Because of the low power requirement of LEDs these leads are often the finest gauge wire. The wire itself acts, under these circumstances, as a minor contribution to heat removal. Increasing the mass of this wire allows it to act as both an electrical conductor and a thermal conductor. The electrical and thermal properties of most materials are well established, so that making a selection for the dual lead/heatsink is predicated on cost, for specific performance.

There have been a number of advances in illumination devices useful for localized medical examinations and procedures. For example, U.S. Pat. No. 9,918,802 to Coppersmith et al. discloses a compact surgical lighting device having a LED with a heat transfer pad, and a flexible circuit. However, the prior art does not address the need for effective heat transfer from the LED and away from the surgical site. The prior art also has limitations in heat and electrical conductivity, which requires additional, and often ineffectual, elements to help route heat away from the site and route electricity to the LED.

Miniaturization of illumination sources is very desirable in surgical cavities where space can be highly limited and illumination sources can occupy valuable space. Illumination sources may also obscure lines of sight for the surgeon and assistants, thereby increasing the importance of miniaturization.

As long as the dual electric heat sink elements, as described herein, maximize the departure of heat from the light assembly, the invention does not require that each element be similar in size. For example, one electrode can occupy most of the cross-sectional area, and the second having very little cross-sectional area, as long as together they both conduct electricity, and maximally conduct heat away from the generation source. An example being a cylinder and a very fine wire running next to or embedded in the cylinders surface.

While the configurations favor thermal conduction away from the source, active convection can be introduced through axial, or otherwise embedded or integrated channels in the heat sink, or created in the heat sink assembly by the proximation of the individual parts. In this way a channel with appropriately propelled gas, liquid, or fluid could further dissipate heat in the surgical field. The channels may also removed smoke, gases, or fluids from the cavity as well as introduce a variety of fluids to the surgical cavity.

SUMMARY OF THE INVENTION

The invention provides a surgical lighting system comprising a body. The body further includes at least one electrically conductive heat sink and at least one light source. The at least one light source may be connected to the at least one heat sink. The body may further include a lens assembly at a distal end. The at least one light source may be positioned between the at least one heat sink and the lens assembly.

A power source may be connected to at least one light source via the at least one heat sink. The at least one heat sink may be directly electrically connected the power source. The at least one light source may be a light emitting diode (LED). The LED may have a first electrode and a second electrode. The at least one heat sink may be electrically connected to one of the first electrode or the second electrode. An electrical conduit may be electrically connected to the other of the first or second electrode. The at least one heat sink may dissipate heat away from the LED.

The at least one heat sink may include a first heat sink, a second heat sink, and an insulator which separates the first and second heat sink. The first heat sink may be electrically connected to the first electrode and the second heat sink may be electrically connected to the second electrode. The first heat sink, the second heat sink, and the LED may complete electrical circuit with a power source. The first heat sink and/or the second heat sink may be capable of dissipating heat away from the LED.

In an embodiment a surgical lighting system may include a body. The body may include a first heat sink with a first outer perimeter and a first distal end. A second heat sink having a second outer perimeter and a second distal end. The second heat sink may be separated from the first heat sink by an insulator. The first heat sink and the second heat sink may be shaped to be complementary such that the first outer perimeter and the second outer perimeter are alignable with each other. A light source may be electrically connected to the first heat sink and the second heat sink so that heat from the light source can be dissipated away by the first heat sink and the second heat sink.

The light source may include a first electrode electrically connected to the first distal end and a second electrode electrically connected to the second distal end. The embodiment may include a power source connected to the first and second heat sinks. The first and/or the second heat may include a channel. The first heat sink may include a recess and the second heat sink may have a shape complementary to the recess. The second heat sink may be capable of nesting in the recess, which aligns the first outer perimeter with the second outer perimeter.

The light source may be a plurality of LEDs. Each LED may include a first electrode and a second electrode. Each first electrode may be electrically connected to the first distal end and each second electrode may be electrically connected to the second distal end. The embodiment may include a power source electrically connected to the first heat sink and the second heat sink. An electrical circuit may be created between the power source and the plurality of LEDs. The first heat sink and the second heat sink may be capable of conducting power to the plurality of LEDs and drawing heat away from the LEDs. The embodiment may dissipate the heat through the first heat sink and the second heat sink.

In an embodiment, a surgical lighting system may include a plurality of heat sinks electrically separated from each other and connected to a power source. The embodiment may include a plurality of light sources. Each of the plurality of light sources may include a first electrode and a second electrode. Each of the plurality of light sources may be electrically connected to at least two of the plurality of heat sinks. The plurality of heat sinks may be configured to conduct power from the power sources to the plurality of light sources and dissipate heat away from the plurality of light sources.

The plurality of heat sinks may include at least one electrically positive heat sink and at least one electrically negative heat sink. The plurality of light sources may include at least two LEDs, each having a first electrode and a second electrode. All of the first electrodes may be connected to the at least one electrically positive heat sink and all of the second electrodes may be connected to the at least one electrically negative heat sink. The at least one electrically positive heat sink and the at least one electrically negative heat sink each further may include channels capable of increasing heat dissipation. The channels may be capable of increasing heat dissipation and/or allowing fluid to flow in an open and/or closed system The plurality of heat sinks may include a positive heat sink and two negative heat sinks. The positive heat sink may be separated from the negative heat sinks by an insulator. The plurality of light sources may include two LEDs, each having a first electrode and a second electrode. Both of the first electrodes may be electrically connected to the positive heat sink, and each of the second electrodes may be electrically connected to one of the negative heat sinks.

BRIEF DESCRIPTION OF THE DRAWINGS

The foregoing and other objects, features and advantages of particular embodiments of the disclosure will be apparent from the following description, as illustrated in the accompanying drawings. The drawings are not necessarily to scale; emphasis instead being placed upon illustrating the principles of various disclosed embodiments.

DETAILED DESCRIPTION OF THE INVENTION

I. Introduction

The present invention will now be described more fully hereinafter with reference to the accompanying drawings. The below embodiments are provided by way of example so that this disclosure will be thorough and complete, and will fully convey the scope of the invention to those skilled in the art. Like numbers refer to like elements throughout.

A heat sink is generally required to dissipate heat away from LED emitters. This ensures the longevity of the emitter and also safeguards the user and surroundings from excessive heat.

The invention consists of a thermally and electrically conductive heat sink that is split in two and isolated in order to prevent electrical conduction between each element (short-circuit) but allow thermal conduction. By welding the LED directly to the heat sink and taking advantage of the electrically conductive properties of the heat sink it minimizes components, simplifies design and construction, and saves room in the assembly. Welding the LED to the heat sink also maximizes the efficiency of the heat sink by filling the available space with only heat sink. This allows for the miniaturization, automation, and simplification of the assembly. The dielectric material may be either rigid or malleable. The heat sink elements may be rigid or malleable. The invention allows construction of light emitting geometries which include multiple LEDs each of which can have orientations advantageous to the user's case, whereby an orientation may be set by the angle of the surface of the heat sink.

Figure 1A:
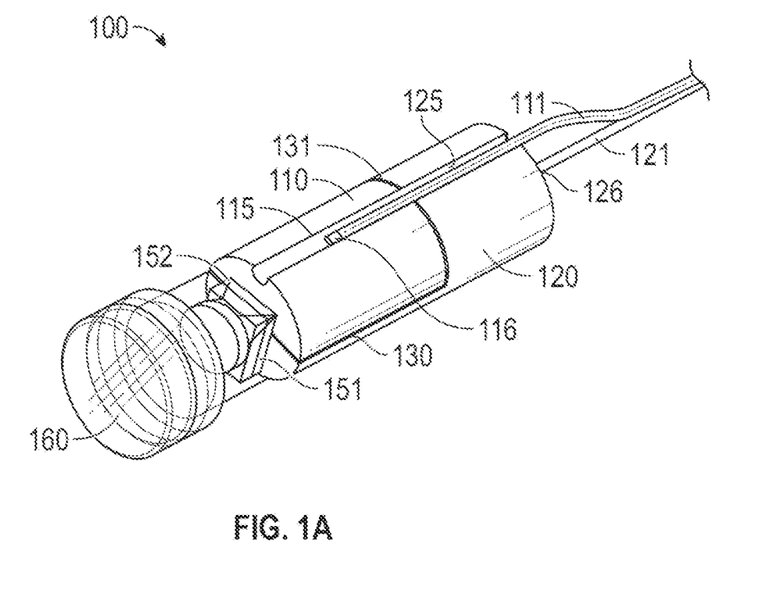
FIG. 1A is a view of an assembled lighting device with two nesting heat sinks acting as electrical conduits.
Figure 1B:
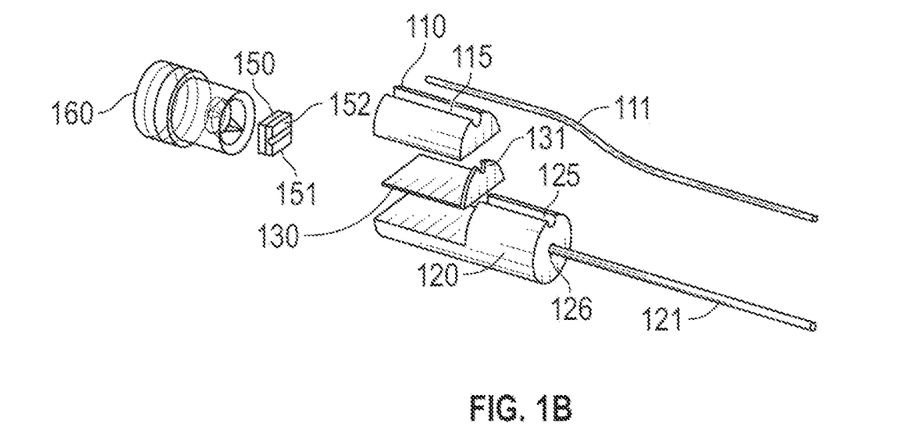
FIG. 1B is an illustration of an exploded perspective of the lighting device in FIG. 1A.

Turning to FIGS. 1A and 1B, a lighting system 100 having an LED 150 connected to dual heat sinks 110 120 acting as electrical conduits. The system 100 includes the LED assembly 150 directly and electrically connected two heat sinks 110 120. Beginning with the heat sinks 110 120, the first heat sink 110 is configured to nest within a complimentarily shaped recess in the second heat sink 120. When nested, the first heat sink 110 fills the recess in the second heat sink 120, which maintains the cylindrical shape of the proximal end of the second heat sink 120. Although the second heat sink 120 is shown having a cylindrical shape, it is envisioned that the first 110 and second 120 heat sink make take any reasonable shape, which is effective for the purpose of the lighting system 100. Reasonable shapes may have a cross-section of a square, triangle, oval, or other polygon, or a mixture of shapes and cross-sections.

The first 110 and second 120 heat sinks are separated by an electrical insulator 130 or dielectric. The insulation electrically separates the first 110 and second 120 heat sink so that no charge may pass between the heat sinks. As shown in FIG. 1B, the insulator 130 is shaped to lie flat between axial complementary sides of the first 110 and second 120 heat sinks. The insulator 130 also has a transverse section 131 which electrically separates the first 110 and second 120 heat sinks in a transverse (to axial) direction. The insulator 130 131 may take any shape which effectively separates the heat sinks, regardless of the shape or size of the heat sinks. Electrical conduits, wires, or heat sinks may be insulated with polyethylene, crosslinked polyethylene (either through electron beam processing or chemical crosslinking), PVC, Kapton, rubber-like polymers, oil impregnated paper, Teflon, silicone, modified ethylene tetrafluoroethylene (ETFE), diamond-like carbon coating, ABS, acetate, acrylic, beryllium oxide, ceramic, Delrin, epoxy, fiberglass, glass, Kynar, Lexan, Merlon, melamine, mica, neoprene, nylon, PET, phenolics, polyester, polyolefins, polystyrene, polyurethane, or any other electrically inert material. The best material will either be an efficient thermal conductor and/or effective, at a very small thickness, to maximize the overall conductivity relative to its cross section.

Each of the heat sinks 110 120 are connected to electrical conduits 111 121, which in this embodiment are electrical wires 111 121. The electrical wires 111 121 are electrically connected to each respective heat sink 110 120, in order to provide a path for electricity to flow, from a power source (not shown) to the LED 150. Electrical wire 111 extends through a groove 125 on the second heat sink, through a notch in the insulator 131, and into a groove 115 on the first heat sink. The wire 111 is electrically connected to the first heat sink 110 in or along the groove 115 at a first location 116. This configuration has at least two benefits: first, the grooves 115 125 allow the wire 111 to rest beneath an outer circumference of both heat sinks 110 120, allowing the assembled LED system 100 to have a regular and compact profile, as shown in FIG. 1A. Second, the first groove 115 allows an electrical connection of the wire 111 to the first heat sink 110, which remains beneath the outer circumference and profile of the system 100. The electrical connection between the wire 111 and the heat sink 110 allows the heat sink 110 to act as an electrode. The second wire 121 is electrically connected at a location 126 on the proximal end of the second heat sink 120. The exact location of the connection 126 may be anywhere on a proximal end of the second heat sink 120, in order to stay within the outer circumference of the assembly 100. The connection allows the second heat sink 120 to also act as an electrode. The insulator 130, 131 prevents any electrical charge from crossing between the heat sinks 110, 120. The insulator 130 may be highly thermally conductive to facilitate the dissipation of heat from the small first 110 heat sink to the more massive second 120 heat sink. The electrical conduits may be of other shapes, sizes, and materials suitable for the shape and size of the light and heat sink system 100.

Heat sinks, electrical conduits, and wires may be constructed of common material like copper but may also be made of any electrical and heat conducting materials, such as gold, silver, aluminum, tungsten, or similar materials. Conduits may be made of elements that efficiently conduct electricity but not heat, such as carbon. Conduits may be made of elements that conduct heat well but not electricity, such as ceramics.

The embodiment 100 also includes a LED assembly 150, including a first electrode 151 and a second electrode 152. In the embodiment shown in FIGS. 1A and 1B, the LED 150 is electrically and physically connected to the first 110 and second 120 heat sinks, so that the first 110 and second 120 heat sinks provide the power or create a circuit to illuminate the LED 150. The arrangement of the first 111 wire and first 110 heat sink and first LED electrode 151 may be an anode or cathode, a ground or have positive voltage. The arrangement of the second 121 wire and second 120 heat sink and second LED electrode 152 may be an anode or cathode, a ground or have positive voltage in accordance with the polarity of current flow for that LED. The first 151 and second 152 electrodes on the LED 150 are separated by a gap of space or another dielectric or insulating material, in order to prevent shorting between the heat sinks 110 120 or the LED electrodes 151, 152.

A preferred light source 150 is a light emitting diode (LED) such as commercially available models that emits high intensity white light and is highly power-efficient. In the present context this means that the preferred lighting, being white, optimizes the user surgeon's viewing and makes minimal demands on the power source, typically compact, lightweight, single use or rechargeable, power cells or batteries. Other energy efficient light sources that may be used in this and any of the intended embodiments further include organic light emitting diodes (OLEDs), or other contemplated compact light sources.

The assembled system 100 also may include a lens assembly 160, which is positioned at the distal end of the system 100. The lens assembly 160 directs and transmits the light emitted by the LED 150 to the user's preferred location. The entire light assembly 100 may be assembled and surrounded by an outer sheath 430 440. The outer sheath 430 440 may be constructed of any suitable material to protect the user, the patient, and the assembly 100.

Figure 2A:
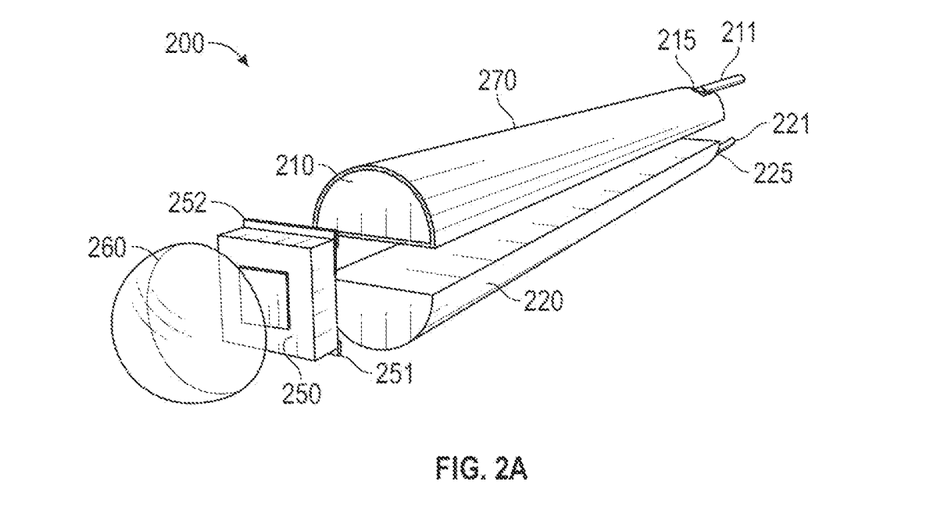
FIG. 2A is a front-plan exploded illustration of a lighting device having a split dual heat sink.
Figure 2B:
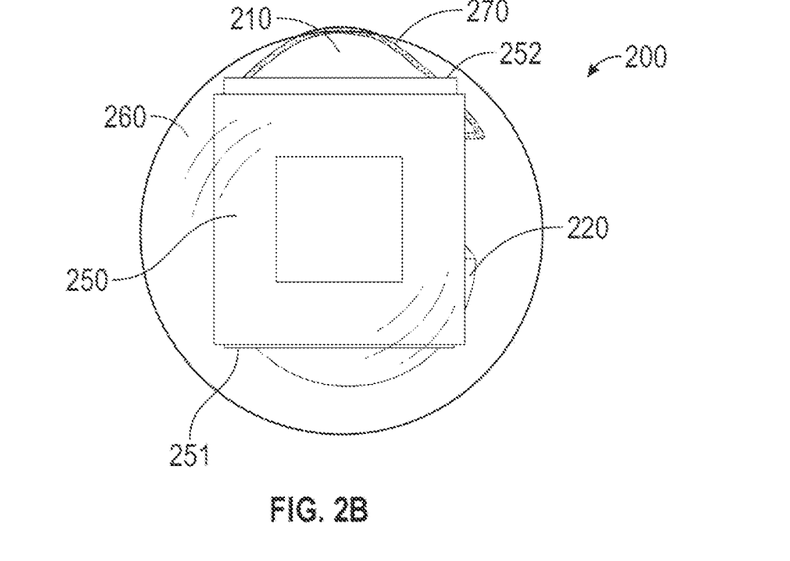
FIG. 2B is a distal end view of the lighting device in FIG. 2A.

Referring to an embodiment depicted in FIGS. 2A and 2B, a light system with a split heat sink system 200 is shown. The system 200 has two electrically isolated heat sinks, a first heat sink 210 and a second heat sink 220. In this embodiment, the two heat sinks 210 220 have complementary shapes that together create a generally cylindrical shape. The first 210 and second 220 heat sinks have opposite semi-circular cross sections, which are intended to rest together along the longitudinal and flattened sections. Although the assembled system 200, is shown having a cylindrical shape, it is envisioned that the first 210 and second 220 heat sink make take any reasonable shape effective for the purpose of the lighting system 200. Reasonable shapes may have a cross-section of a square, triangle, oval, or other polygon, or a mixture of shapes and cross-sections, including ones which might nest.

In this embodiment, the first 210 heat sink is encapsulated on the majority of its surface area with an insulator 270. Notably, the insulator 270 electrically separates the first heat sink 210 from the second heat sink 220. The insulator may be thermally conductive to help dissipate heat from either of the first 210 or second 220 heat sink to the other heat sink. Because the insulator may add size to the first heat sink 210, the first heat sink 210 may be manufactured slightly smaller than the second heat sink 220. With a smaller first 210 heat sink, when the insulator 270 is applied, the first heat sink 210 may duplicate the external size parameters of the uninsulated second heat sink 220, so that when assembled, the system 200 will have a uniform outer circumference.

The system 200 has a first electrical conduit 211, or a wire, electrically connected to the first 210 heat sink at a first contact location 215. An electrical connection made at a first contact location 215 allows electricity to pass from the first wire 211 to the first 210 heat sink; thus making the first 210 heat sink an electrode. The insulator 270 may or may not cover the first contact location 215. The insulator 270 may extend from the first 210 heat sink and onto and over the wire 211. The system 200 has a second electrical conduit 221, or a wire, electrically connected to the second 220 heat sink at a second contact location 225. This electrical connection 225 allows electricity to pass from the first wire 221 to the first 220 heat sink; thus making the first 220 heat sink an electrode.

The system 200 also includes a LED assembly 250, including a first electrode 251 and a second electrode 252. In the system shown in FIGS. 2A, the LED 250 is directly electrically and physically connected to the first 210 and second 220 heat sinks, so that the first 210 and second 220 heat sinks provide the power to illuminate the LED. The arrangement of the first 211 wire and first 210 heat sink and first LED electrode 251 may be an anode or cathode, a ground or provide positive voltage. The arrangement of the second 221 wire and second 220 heat sink and second LED electrode 252 may be an anode or cathode, a ground or provide positive voltage. The first 251 and second 252 electrodes on the LED 250 are separated by a gap of space or another dielectric or insulating material, in order to prevent shorting between the heat sinks 210, 220 or the LED electrodes 251, 252. A preferred light source 250 is a light emitting diode (LED) such as commercially available models that emits high intensity white light and is highly power-efficient. In the present context this means that the preferred lighting, being white, optimizes the user surgeon's viewing and makes minimal demands on the power source, typically compact, lightweight, single use or rechargeable, power cells or batteries. An alternative color may be selected to favor transillumination of tissue.

The assembled system 200 also may include a lens assembly 260, which is positioned at the distal end of the system 200. The lens assembly 260 directs and transmits the light emitted by the LED 250 to the user's preferred location. The entire light assembly 200 may be assembled and surrounded by an outer sheath 430 440. The outer sheath 430 440 may be constructed of any suitable material to protect the user, the patient, and the assembly 200.

FIG. 2B is a distal perspective of the system 200, illustrating a cylindrical design of the assembly. The lens 260 is shown as the distal portion of the system 200, in which the first 210 and second 220 heat sinks are masked by the lens. In some embodiments of system 200, the first 210 and second 220 heat sinks may remain separated after final assembly of the system 200. Additional thermally conductive and electrically non-conductive material may be placed between the first 210 and second 220 heat sinks. The insulator 270 is shown covering the first 210 heat sink. The LED 250 is shown distally behind the lens 260. FIG. 2B shows an alternative wherein the second electrode 252 is contacting the first 210 heat sink and the first electrode 251 is contacting the second 220 heat sink.

In this embodiment, wherein the first heat sink 210 and the second heat sink 220 have a hemi-cylindrical shape, the may be created by splitting a cylindrical element into symmetrical halves. The semi-cylindrical or D-shaped first heat sink 210 and second heat sink 220 may be formed by flattening a side of a cylindrical element. The first contact location 215 may be a groove, indentation, or other space or location on the first heat sink 210. The first contact location 215 may be milled or pressed so that the first contact location 215 is depressed from the surface and into the first heat sink 210. Similarly, the second contact location 225 may be a groove, indentation, or other space or location on the second heat sink 220. The second contact location 225 may be milled or pressed so that the second contact location 225 is depressed from the surface and into the second heat sink 220. The first electrical conduit 211 and the second electrical conduit 221 may be connected to the first contact location 215 and the second contact location 225 by welding, soldering, crimping, or other means securing the wires to the heat sinks and allowing electricity to flow.

The first heat sink 210 and the second heat sink 220 both may be unencapsulated by an insulator 270 or dielectric. In such a configuration, the first heat sink 210 and the second heat sink may be separated by an adhesive. The adhesive provides electrical isolation of the heat sinks and also secures the first heat sink 210 together with the second heat sink 220. The securement of the heat sinks together allows for an improvement in assembly and manufacturing. When assembling on a small or miniature scale, the connection of an LED 250 may be simpler when the anode and cathode (heatsinks 210 220) cannot move relative to one another. With the first heatsink 210 and the second heat sink 220 are fixed together, it is easier to line up and electrically attach the first electrode 251 and the second electrode 252.

The first heat sink 210 and the second heat sink 220 both may be unencapsulated by an insulator 270 or dielectric. In such a configuration, the first heat sink 210 and the second heat sink 220 may be separated by an adhesive. The adhesive provides electrical isolation of the heat sinks and also secures the first heat sink 210 together with the second heat sink 220. The securement of the heat sinks together allows for an improvement in assembly and manufacturing. When assembling on a small or miniature scale, the connection of an LED 250 may be simpler when the anode and cathode (heatsinks 210 220) cannot move relative to one another. With the first heatsink 210 and the second heat sink 220 are fixed together, it is easier to line up and electrically attach the first electrode 251 and the second electrode 252.

Figure 3A:
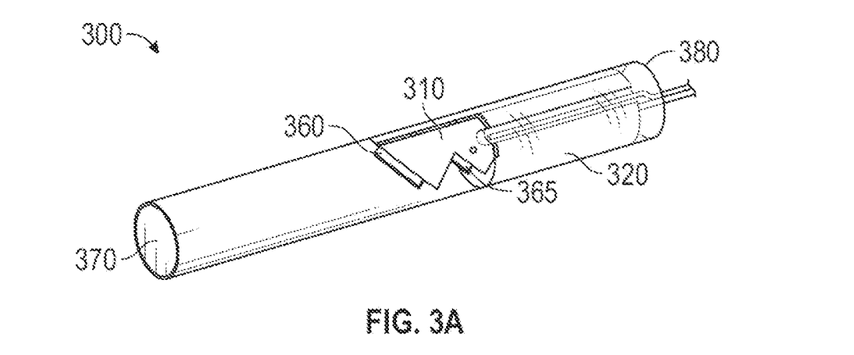
FIG. 3A is a side plan illustration of a lighting device with multiple LEDs and nesting heat sinks.
Figure 3B:
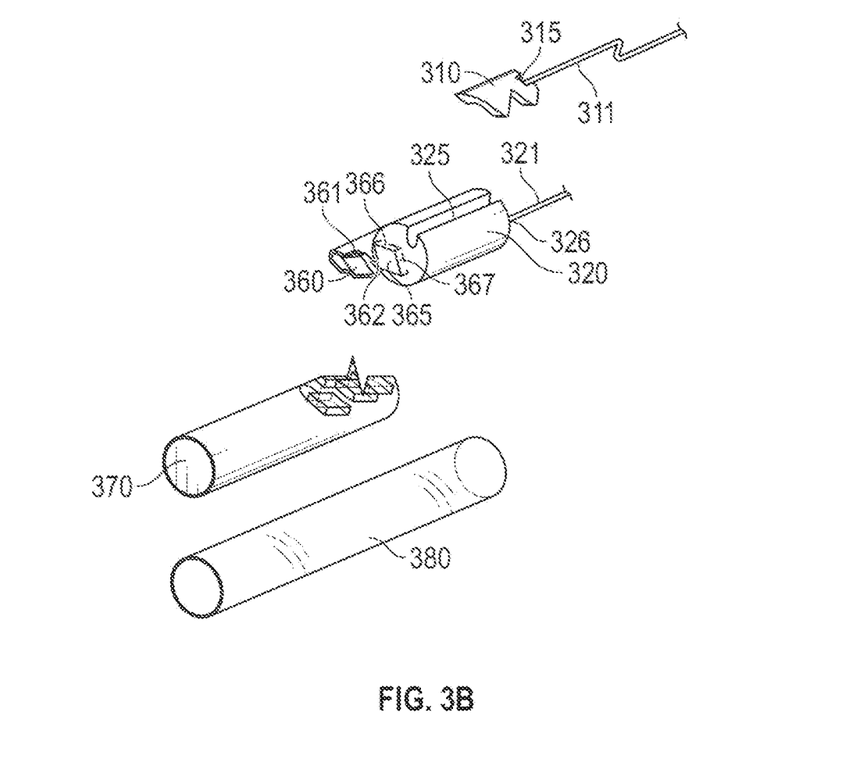
FIG. 3B is a side plan illustration of an exploded view of the lighting device in FIG. 3A.

Turning to FIG. 3A and FIG. 3B, an embodiment is depicted as a multiple LED dual heat sink system 300. The system 300 includes two or more LEDs 360 365 connected to multiple heat sinks 310 320, acting as powered electrodes. The system 300 has a first small heat sink 310 and a second larger heat sink 320. The first 310 heat sink having a shape complementary to a recess or cut out in the second 320 heat sink. In the embodiment shown in FIG. 3, the first 310 heat sink has a stepped configuration configured to nest within the second 320 heat sink and create a plurality of locations to which a LED 360 365 may electrically contact, via respective first electrodes 361 366. The electrical contact locations are on distal portions of the stepped configuration. The second 320 heat sink has a complementary-shaped stepped configuration, which allows the first 310 heat sink to nest within the second 320 heat sink. The second 320 heat sink has an axial extension which provides support for two LEDs 365 366. The support extension also provides an electrical connection to a second electrode 362 367.

The system 300 is shown assembled having a generally cylindrical shape, when first 310 and second 320 heat sinks are nested. Although the assembled system 300, is shown having a cylindrical shape, it is envisioned that the assembled first 310 and second 320 heat sinks make take any reasonable shape effective for the purpose of the lighting system 300. Reasonable shapes may have a cross-section of a square, triangle, oval, or other polygon, or a mixture of shapes and cross-sections.

System 300 may include an insulator 371 that electrically separates the first 310 and second 320 heat sinks. The insulator may cover the first 310 heat sink or the insulator may be a separate element that is present only at the interface between the first 310 and second 320 heat sinks. Other configurations of the insulator are contemplated, which electrically separate the first 310 and second 320 heat sinks and maintain an appropriate cross section and/or diameter of the assembled system 300.

The first 310 heat sink may have a first electrical conduit 311, or wire, electrically attached or coupled to a proximal location 315. This connection 315 allows electricity to flow from the wire 311 to the first 310 heat sink. The second 320 heat sink has a groove 325 along the outer surface in a longitudinal direction. The groove 325 allows the wire 311 to run along the second 320 heat sink to the first connection location 315, without affecting the general outer circumference of the second 320 heat sink. A second electrical conduit 321, or wire, is electrically attached or coupled to the second 320 heat sink at a second proximal connection location 326. The connection 326 allows electricity to flow from the wire 321 to the second 320 heat sink.

The system 300 has at least two LEDs 360 365 arranged in a staggered position on the second 320 heat sink. The LEDs 360 365 are directed so that the distal LED does not obscure the light emitted from the proximal LED. The orientation of the LEDs 360 365 may allow the light to emit in a broad, sideways manner, or the light may be summed and focused via a waveguide or other light affecting means to combine and shine in a longitudinal direction, axial to the system 300. The LEDs 360 365 each have first electrodes 361 366 and second electrodes 362 367. In a contemplated arrangement, the first electrodes 361 366 may be electrically connected to the first 310 heat sink and the second electrodes may be electrically connected to the second 320 heat sink. Alternatively, the electrodes may be connected to the other heat sink.

The system 300 includes a lens assembly 370, which is positioned at the distal end of the system 300. The lens assembly 370 directs and transmits the light emitted by the LEDs 360 365 to the user's preferred location. The entire light assembly 300 may be assembled and surrounded by an outer sheath 380. The outer sheath 380 may be constructed of any suitable material to protect the user, the patient, and the assembly 300.

Figure 4:
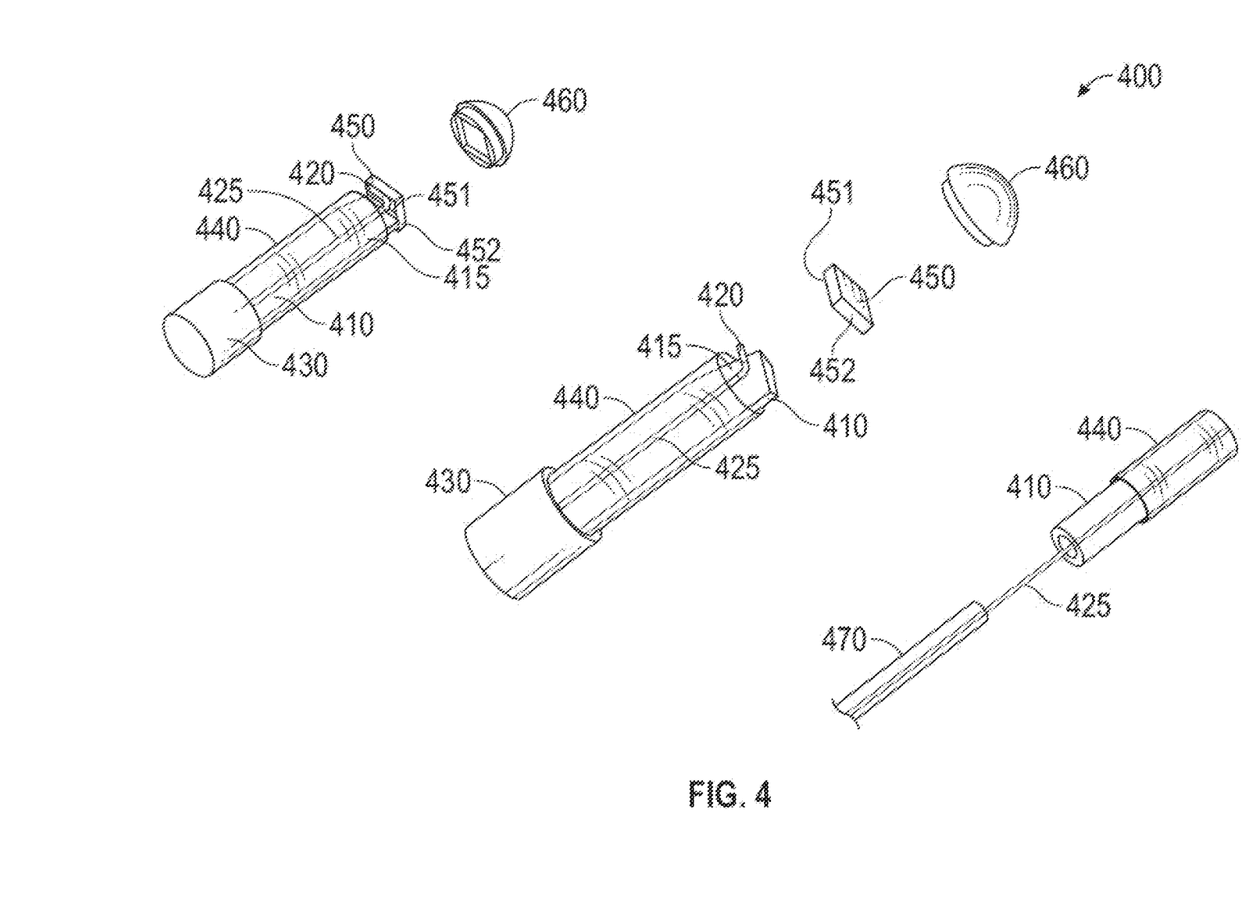
FIG. 4 is a side plan illustration of a lighting device having a heat sink as an electrical conduit and electrically connected to a LED.

Referring to FIG. 4, a LED system 400 having a heat sink electrode is shown. The system 400 includes a heat sink 410 having a distal end 415 and an electrode 420. The electrode 420 may be wrapped in an insulator 425 to separate it from the heat sink 410. The heat sink 410 and the electrode 420 are electrically connected to an LED assembly. The heat sink 410 operates as a second electrode to allow electricity to flow from a power source (not shown) and between the heat sink 410, the LED 450, and the electrode 420. The heat sink 410 electrically connects with the first LED electrode 451. The electrode 420 electrically connects with the second LED electrode 452. Depending on the orientation of the LED assembly, the heat sink 410 can electrically connect to the second LED electrode 452 and the electrode 420 can electrically connect to the first LED electrode 451.

The heat sink 410 is shown having a generally cylindrical shape with a tapered distal end 415. The distal end 415 is tapered to a shape which may generally complement the shape of either LED electrode 451 452. FIG. 4 shows the electrode 420 having an insulator which electrically separates the electrode 420 from the heat sink 420. Alternatively, the heat sink 420 may be, additionally or individually, encased by an insulator. FIG. 4 also shows an outer or secondary insulator 470, which may be around the electrode 420 or the heat sink 410.

The system 400 includes a lens assembly 460, which is positioned at the distal end of the system 400. The lens assembly 460 directs and transmits the light emitted by the LED assembly 450 to the user's preferred location. The entire light assembly 400 may be assembled and surrounded by an inner sheath 440 and an outer sheath 460. The inner 440 and outer 430 sheaths may be constructed of any suitable material to protect the user, the patient, and the assembly 400, such as a dielectric or insulating material to prevent shorting, or a metal to provide the device with structural rigidity.

An alternative embodiment of system 400 contemplates the heat sink 410 with a hollow cavity extending through the length of the heat sink 410. A second heat sink (not shown) may be arranged inside the first heat sink 410, extending from a proximal to distal end. The first heat sink 410 and the second heat sink nest in a concentric orientation; the first heat sink 410 is a hollow cylinder and the second heat sink is a separate core. The first heat sink 410 and the second heat sink may be electrically separated by an insulator. At least one LED may be electrically connected to the distal ends of the first 410 and second heat sinks. This alternative system 400 may have multiple LEDs electrically connected to the distal ends of the first 410 and second heat sinks in a starburst-like pattern. One of the heat sinks would act as a ground and the other heat sink provides a positive voltage. The multiple LEDs may be arranged to have different colors, hues, directions, or intensity.

Figure 5:
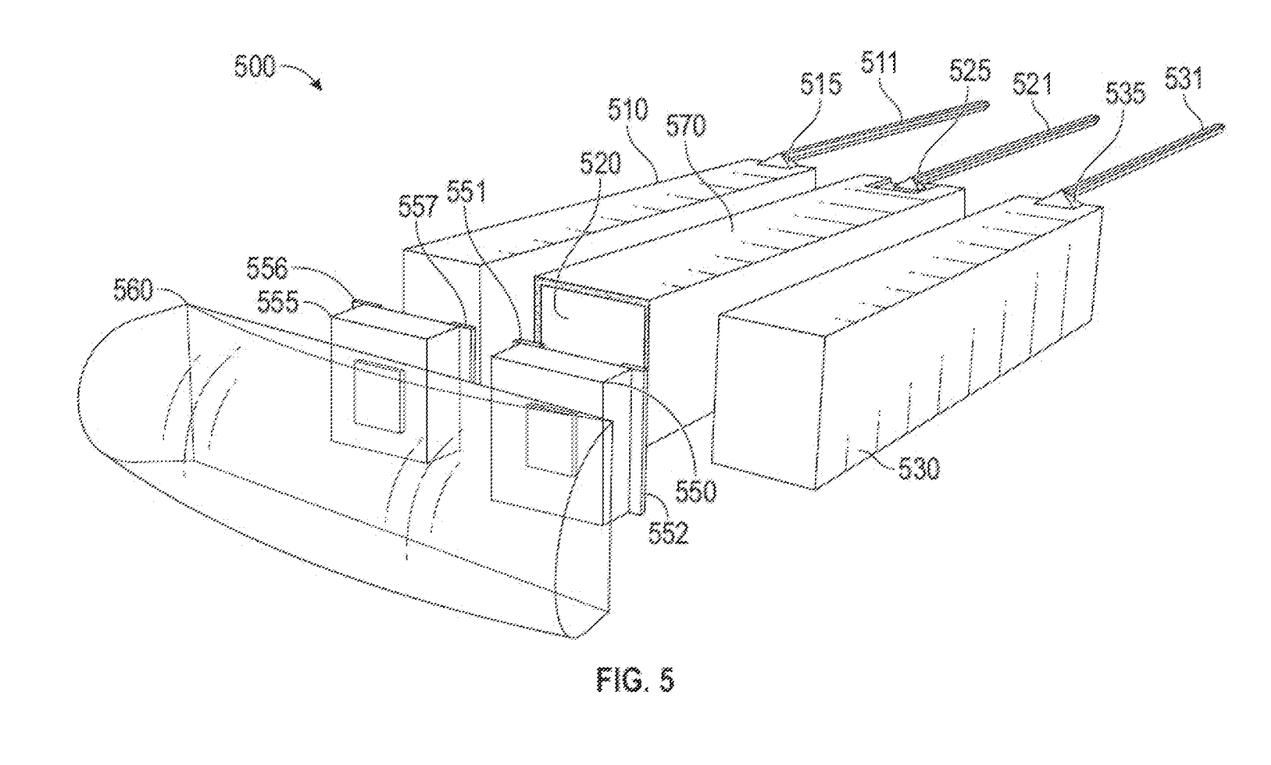
FIG. 5 is a front plan view of an LED system with a plurality of heat sinks and a plurality of LEDs.

Referring to FIG. 5, an embodiment of an LED system 500 with a plurality of heat sinks is shown. The system is a parallel arrangement of LEDs utilizing a single heat sink 520 having a first charge, and two heat sinks 510 530 having the opposite charge from the single heat sink 520. Assuming the single heat sink 520 acts as the positive wire, the two heat sinks 510 530 act as the negative wire. The system utilizes power from a power supply (not shown) to energize the LEDs. A first heat sink 510 is electrically connected to a first electrical conduit 511 or wire at electrical connection location 515. A second heat sink 520 is electrically connected to a second electrical conduit 521 or wire at electrical connection location 525. A third heat sink 530 is electrically connected to a third electrical conduit 531 or wire at electrical connection location 535.

When LEDs are spanned across and electrically connected to the single heat sink 520 and either of the two heat sinks 510 530, a circuit is created, and the LED is activated. System 500 provides for two LEDs 550 555 each electrically connected to the single heat sink via a first LED electrode 551 557. The first LED 550 is also electrically connected to one of the two heat sinks 530 via an LED electrode 552, completing a circuit using heat sinks 530 520. The second LED 555 is also electrically connected to the other of the two heat sinks 510 via an LED electrode 556, completing a circuit using heat sinks 510 520.

At least one of the heat sinks is covered by an insulator 570. FIG. 5 shows heat sink 520 covered by an insulator, which allows the oppositely charged heat sinks 510 530 to rest against the electrically "hot" heat sink 520, meaning there is a voltage across the heat sink 520. In order to maintain an even outer perimeter of the assembled system 500, heat sink 520 is slightly smaller to make up for the thickness of the insulator 570. The insulator may have an additional cut-out or section to allow for the second electrical connection. Alternatively, a center heat sink 520 may be a ground terminal or electrode, and the flanking heat sinks 510 530 may supply a positive voltage.

System 500 may be assembled having a generally rectangular shape, when all heat sinks 510 520 530 are assembled next to one another. Although the assembled system 500, may have a rectangular shape, it is contemplated that the assembled heat sinks 510 520 530 make form any reasonable shape effective for the purpose of the lighting system 500. Reasonable shapes may have a cross-section of a square, triangle, oval, or other polygon, or a mixture of shapes and cross-sections. System 500 is shown with three heat sinks 510 520 530, but any number of heat sinks may be assembled together in series to energize any number of electrically connected LEDs. An advantage of this system 500 is that the arrangement provides a flat low-profile light source, which might also be used to follow the contour of a surgical instrument or its surface.

Figure 6:
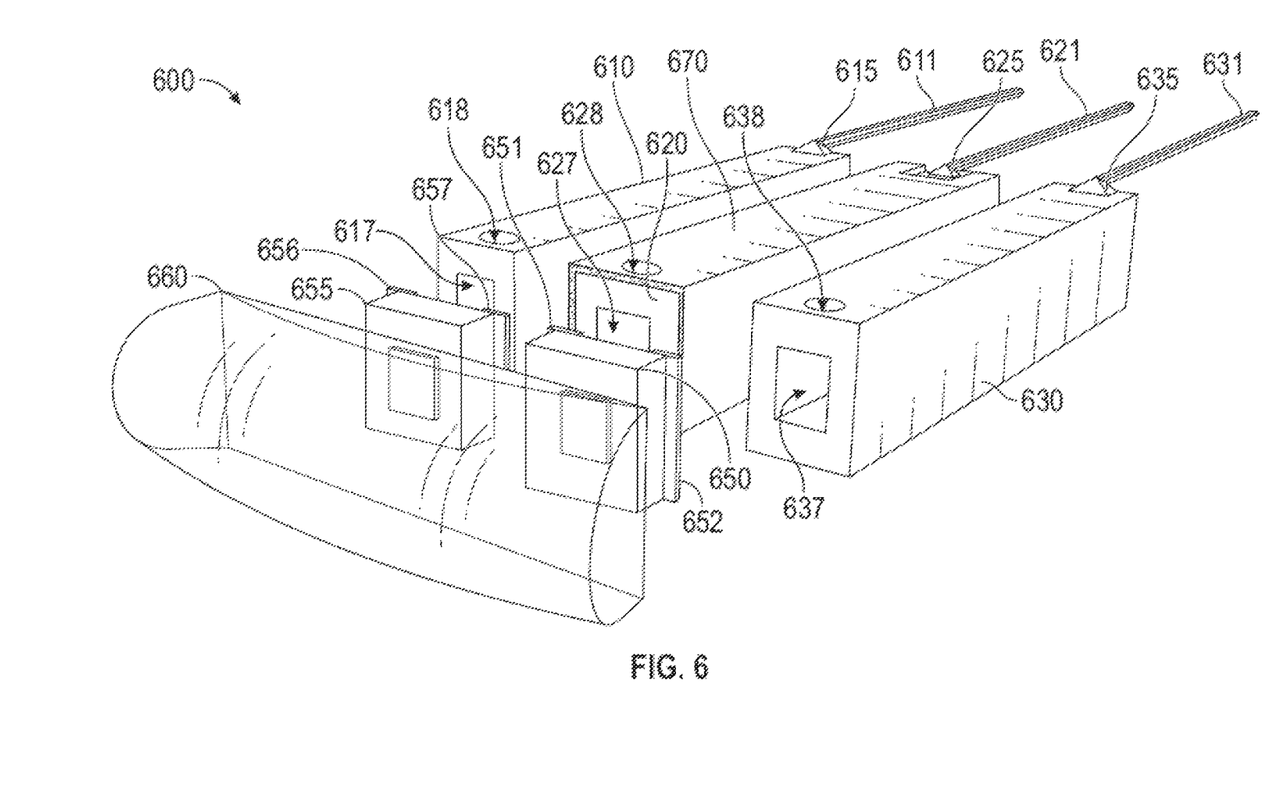
FIG. 6 is a front plan view of an LED system with a plurality of heat sinks having cavities and a plurality of LEDs.

Referring to FIG. 6, an embodiment of an LED system 600 with a plurality of heat sinks, having ventilation channels is shown. Similar to the embodiment shown in FIG. 5, FIG. 6 shows system is a parallel arrangement of LEDs utilizing a single heat sink 620 having a first charge, and two heat sinks 610 630 having the opposite charge from the single heat sink 620. Assuming the single heat sink 620 acts as the positive wire, the two heat sinks 610 630 act as the negative wire. The system utilizes power from a power supply (not shown) to energize the LEDs. A first heat sink 610 is electrically connected to a first electrical conduit 611 or wire at electrical connection location 615. A second heat sink 620 is electrically connected to a second electrical conduit 621 or wire at electrical connection location 625. A third heat sink 630 is electrically connected to a third electrical conduit 631 or wire at electrical connection location 635.

When LEDs are spanned across and electrically connected to the single heat sink 620 and either of the two heat sinks 610 630, a circuit is created, and the LED is activated. System 600 provides for two LEDs 650 655 each electrically connected to the single heat sink via a first LED electrode 651 657. The first LED 650 is also electrically connected to one of the two heat sinks 630 via an LED electrode 652, completing a circuit using heat sinks 630 620. The second LED 655 is also electrically connected to the other of the two heat sinks 610 via an LED electrode 656, completing a circuit using heat sinks 610 620.

At least one of the heat sinks is covered by an insulator 670. FIG. 6 shows heat sink 620 covered by an insulator, which allows the oppositely charged heat sinks 610 630 to rest against the electrically "hot" heat sink 620, meaning there is a voltage across the heat sink 620. In order to maintain an even outer perimeter of the assembled system 600, heat sink 620 is slightly smaller to make up for the thickness of the insulator 670. The insulator may have an additional cut-out or section to allow for the second electrical connection. Alternatively, a center heat sink 620 may be a ground terminal or electrode, and the flanking heat sinks 610 630 may supply a positive voltage.

Lighting system 600 includes heat sinks 610 620 630, each having ventilation channels running axially through the body of the heat sink. The first heat sink 610 has a ventilation channel 617 which extends between the distal and proximal ends of the heat sink 610. The second heat sink 620 has a ventilation channel 627 which extends between the distal and proximal ends of the heat sink 620. The third heat sink 630 has a ventilation channel 637 which extends between the distal and proximal ends of the heat sink 630. The ventilation channel allows the movement of an gas, liquid, or fluid to further encourage the dissipation of heat from the LED and the distal end of the system 600. The ventilation channels may be in a closed system or an open system. In a closed system, the ventilation channels may be capable of passing a gas, a liquid, or a fluid past or through the heat sinks to draw heat away from the LEDs. Though not specifically depicted, the ventilation channels may be created by the apposition of two or more heat sink elements thereby forming a complete perimeter of the channel.

In an open system, any of the ventilation channels 617 627 637 may be used to remove smoke or other vapors from the surgical cavity. Smoke and vapors may obscure vision of the surgeon and light transmission to achieve certain procedures. The ventilation channels 617 627 637 therefore may accomplish both heat dissipation and smoke evacuation. It is also in the scope of the invention to configure the ventilation channels 617 627 637 to pass fluid directly into the surgical cavity to irrigate the cavity. The ventilation channels 617 627 637 may be used to remove fluid from the surgical cavity. It is also in the scope of the invention to have a mixed open/closed system, whereby only certain ventilation channels are open and others are closed. The ventilation channels 617 627 637 may also be switchable between and open or closed system.

The heat sink 610 may also include an aperture 618 on the top or bottom of the heat sink 610, which may or may not connect and be in fluid communication with the ventilation channel 617. The heat sink 620 may also include an aperture 628 on the top or bottom of the heat sink 620, which may or may not connect and be in fluid communication with the ventilation channel 627. The heat sink 630 may also include an aperture 638 on the top or bottom of the heat sink 630, which may or may not connect and be in fluid communication with the ventilation channel 637. The movement of air or fluid through the ventilation channels 617 627 637 and/or apertures 618 628 638 may be passive or active. It is also contemplated that any of the ventilation channels and/or apertures may be in fluid communication with any of the others (not shown). This arrangement creates a manifold of ventilation channels giving the system 600 user further options in dissipating heat, smoke, or fluid from the distal end of the system 600.

System 600 may be assembled having a generally rectangular shape, when all heat sinks 610 620 630 are assembled next to one another. Although the assembled system 600, may have a rectangular shape, it is contemplated that the assembled heat sinks 610 620 630 make form any reasonable shape effective for the purpose of the lighting system 600. Reasonable shapes may have a cross-section of a square, triangle, oval, or other polygon, or a mixture of shapes and cross-sections. System 600 is shown with three heat sinks 610 620 630, but any number of heat sinks may be assembled together in series to energize any number of electrically connected LEDs. An advantage of this system 600 is that the arrangement provides a flat low-profile light source, which might also be used to follow the contour of a surgical instrument or its surface.

It is contemplated that any of the disclosed or suggested embodiments may include outer coverings that are suitable for appropriate used in a sterile environment. The coverings may securely contain the operational elements of the system and effectively isolate the system from moisture or other environmental factors. The systems disclosed herein may be disposable. The systems disclosed herein may be capable and configured for repeated use in multiple surgeries. The systems disclosed herein may be autoclavable or sterilized by other known means.

It is contemplated that the heat sinks, in any of the systems disclosed here, may have additional heat dissipation means extending further proximally from the system. The additional heat dissipation means may include a length of electrical conduit, hydraulic or pneumatic circulation devices as discussed in relation to system 600, or other reasonable devices or methods.

Optionally, the entire lighting system could be assembled and then, using any suitable known manufacturing technique, encased in a thin, sterile, biocompatible, impermeable coating to form a sealed integral item. Numerous suitable plastics materials for such coatings are known that would provide the desired electrical insulation and the thermal conduction capabilities—as discussed below. Such an assembly would be particularly suitable for more or less standard applications, e.g., in providing lighting during urogynacological, otolaryngological, neurosurgical, or any other types of surgery on patients.

It should be appreciated that an experienced surgeon can derive valuable information from an accurate viewing of a patient's tissues during a surgical procedure. Clear and consistent lighting of tissues of interest is therefore extremely important. White light is considered particularly useful in revealing subtle gradations of color, hue and condition of tissues that may be healthy, traumatized or diseased. It should also be appreciated that the addition of any lighting system to a known surgical tool will inevitably add to the weight and volume of the combination that will have to be manipulated by the user. The present invention in its various embodiments aims to ensure that the lighting system will be as light in weight, and as small in size, as possible in light of available technology and that it will be configured and disposed to be minimally intrusive to the surgeon's field of view. The preferred LEDs will ensure that the preferred white light output will not waver in intensity or color for prolonged periods of use in complex surgery. Other preferred LEDs may produce other colors or wavelengths of light suitable for transillumination procedures and applications.

It should be noted that there may be circumstances when other than white light may be most suitable. There may be applications where it is most convenient to have the light emitted in a forward or a sideways direction relative to the distal end of the invention or any of the embodiments, so that the light be directed in a forward or non-forward direction relative to the distal end of the light system. Lighting for such applications may be best provided via modified forms of the lens and/or LED assembly.

The material for such and other heat sinks ideally should have high heat capacitance, high thermal conductivity, and high electrical conductivity. Practicality and considerations of cost and ease of manufacture will determine the actual shapes, thermal capacitances, masses and sizes of the heat sinks and also determine the choice of pure or alloyed metals such as aluminum, copper, gold, brass, beryllium-copper alloy, platinum or titanium, both for the heat sinks and for the electrical conductors or wires. The heat sinks are essentially only thermally conductive masses to which the inevitable byproduct heat from the light-producing activity flows continuously during operation of the light producing LED or the like. The physical configurations, any electrically insulating materials, and the interconnections between the heat sinks, as persons of ordinary skill in the art will appreciate, should be chosen to facilitate heat transfer without adding unduly to the weight of the lighting system.

It is within the understanding of the invention and embodiments disclosed herein, that the first and/or second heat sinks of any of the systems may be electrically connected to the LED, but physically separated. The electrodes of the LEDs may be electrically connected to the respective heat sinks via an electrical conduit smaller than the full LED electrode. The heat sink may be additionally separated from the LED by a thermally conductive material.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

The invention claimed is:

1. A lighting system comprising:
    a body, having
        at least one electrically conductive heat sink, wherein the at least one heat sink further comprises channels capable of at least one of increasing heat dissipation or allowing fluid to flow in an open or closed system; and
        at least one light source electrically connected to the at least one heat sink.

2. The lighting system of claim 1, the body further comprising a lens assembly at a distal end of the body, wherein the at least one light source is positioned between the at least one heat sink and the lens assembly.

3. The lighting system of claim 1, further comprising a power source connected to the at least one light source via the at least one heat sink.

4. The lighting system of claim 3, wherein the at least one heat sink is directly electrically connected to the power source.

5. The lighting system of claim 1, wherein the at least one light source is a light emitting diode (LED) having a first and a second electrode, wherein the at least one heat sink is connected to one of the first electrode or the second electrode.

6. The lighting system of claim 5, wherein an electrical conduit is electrically connected to the other of the first or second electrode; and wherein the at least one heat sink dissipates heat away from the LED.

7. The lighting system of claim 5, wherein the at least one heat sink includes a first heat sink, a second heat sink, and an insulator separating the first heat sink and the second heat sink.

8. The lighting system of claim 7, wherein the first heat sink is electrically connected to the first electrode and the second heat sink is electrically connected to the second electrode.

9. The lighting system of claim 8, wherein the first heat sink, the second heat sink, and the LED complete an electrical circuit with a power source; and
   wherein the first heat sink and the second heat sink dissipate heat away from the LED.

10. A lighting system comprising:
   a body; the including
      a first heat sink having a first outer perimeter and a first distal end
      a second heat sink having a second outer perimeter and a second distal end, and an insulator separating the second heat sink from the first heat sink;
      wherein the first heat sink and the second heat sink are shaped to be complementary such that the first outer perimeter and the second outer perimeter are alignable, and wherein the first and second heat sinks each comprise channels capable of at least one of increasing heat dissipation or allowing fluid to flow in an open or closed system; and
   a light source electrically connected to the first heat sink and the second heat sink so that heat from the light source is dissipated away.

11. The lighting system of claim 10, wherein the first heat sink further comprises a recess and the second heat sink has a shape complementary to the recess, such that the second heat sink is capable of nesting in the recess which aligns the first outer perimeter with the second outer perimeter.

12. The lighting system of claim 10, further comprising a power source electrically connected to the first heat sink and the second heat sink,
   wherein the light source is a plurality of LEDs, each LED comprising a first electrode electrically connected to the first distal end and a second electrode electrically connected to the second distal end; and
   an electrical circuit created between the power source and the plurality of LEDs with the first heat sink and the second heat sink conducting power to the plurality of LEDs and drawing and dissipating heat away from the LEDs.

13. The lighting system of claim 10, further comprising a power source connected to the first and second heat sinks
   wherein a first electrode of the light source is electrically connected to the first distal end and a second electrode of the light source is electrically connected to the second distal end.

14. The lighting system of claim 13, wherein the at least one heat sink further comprises a channel.

15. A lighting system comprising:
   a plurality of heat sinks electrically separated from each other and connected to a power source; and
   a plurality of light sources including at least two LEDs, each having a first electrode and a second electrode,
   wherein each of the plurality of light sources is electrically connected to at least two of the plurality of heat sinks; and
   wherein the plurality of heat sinks are configured to conduct power from the power source to the plurality of light sources and to dissipate heat away from the plurality of light sources, wherein the plurality of heat sinks includes at least one electrically positive heat sink and at least one electrically negative heat sink,
   wherein the at least one positive heat sink and the at least one negative heat sink each further comprise channels capable of at least one of increasing heat dissipation or allowing fluid to flow in an open or closed system.

16. The lighting system of claim 15, further comprising an insulator,
   wherein the plurality of heat sinks comprises an electrically positive heat sink and two electrically negative heat sinks, the electrically positive heat sink separated from the negative heat sinks by the insulator; and
   the plurality of light sources comprises two LEDs, each having a first electrode and a second electrode, with both of the first electrodes are electrically connected to the electrically positive heat sink, and each of the second electrodes are electrically connected to one of the electrically negative heat sinks.

* * * * *